(12) United States Patent
Mueller et al.

(10) Patent No.: US 8,193,821 B2
(45) Date of Patent: Jun. 5, 2012

(54) SENSOR SYSTEM AND METHODS FOR THE CAPACITIVE MEASUREMENT OF ELECTROMAGNETIC SIGNALS HAVING A BIOLOGICAL ORIGIN

(75) Inventors: Klaus-Robert Mueller, Berlin (DE); Benjamin Blankertz, Berlin (DE); Gabriel Curio, Berlin (DE); Meinhard Schilling, Wolfenbuettel (DE)

(73) Assignees: Fraunhoffer-Gesellschaft zur Foerderung der Angewandten Forschung E.V., Munich (DE); Technische Universitaet Braunschweig, Braunschweig (DE)

( * ) Notice: Subject to any disclaimer, the term of this patent is extended or adjusted under 35 U.S.C. 154(b) by 711 days.

(21) Appl. No.: 11/722,495

(22) PCT Filed: Dec. 23, 2005

(86) PCT No.: PCT/DE2005/002319
§ 371 (c)(1),
(2), (4) Date: Nov. 24, 2009

(87) PCT Pub. No.: WO2006/066566
PCT Pub. Date: Jun. 29, 2006

(65) Prior Publication Data
US 2010/0060300 A1   Mar. 11, 2010
US 2011/0248729 A2   Oct. 13, 2011

(30) Foreign Application Priority Data
Dec. 23, 2004   (DE) .......................... 10 2004 063 249

(51) Int. Cl.
  *G01R 27/26*   (2006.01)
(52) U.S. Cl. ........................................................ 324/686
(58) Field of Classification Search ................... None
  See application file for complete search history.

(56) References Cited

U.S. PATENT DOCUMENTS
6,445,940 B1   9/2002   Gevins et al.
(Continued)

FOREIGN PATENT DOCUMENTS
DE   3510195   9/1986
(Continued)

OTHER PUBLICATIONS

Harland C J et al: "Remote detection of human electroencephalalograms using ultrahigh input impedance electric potential sensors" Applied Physics Letters AIP USA, vol. 81, No. 17, Oct. 21, 2002, pp. 3284-3286.

(Continued)

*Primary Examiner* — Paresh Patel
(74) *Attorney, Agent, or Firm* — Maschoff Gilmore & Israelsen

(57) ABSTRACT

The invention relates to a sensor system and several method for the capacitive measurement of electromagnetic signals having a biological origin. Such a sensor system comprises a capacitive electrode device (10), an electrode shielding element (20) which surrounds the electrode device (10) at least in part in order to shield the same (10) from interfering external electromagnetic fields, and a signal processing device (30) for processing electromagnetic signals that can be detected by means of the electrode device (10). According to the invention, additional shielding means (21) three-dimensionally surround the electrode device (10) and the electrode shielding element (20) at least in part in order to block out interfering external electromagnetic fields. The changes in the electrode capacity of the capacitive sensor system are determined with the aid of several methods which particularly use the inventive sensor system in order to take said changes into account when the test signals are evaluated.

31 Claims, 9 Drawing Sheets

U.S. PATENT DOCUMENTS

| | | | |
|---|---|---|---|
| 6,807,438 B1 | 10/2004 | Brun Del Re et al. | |
| 6,961,601 B2 * | 11/2005 | Matthews et al. ............. | 600/372 |
| 2003/0036691 A1 | 2/2003 | Stanaland et al. | |
| 2004/0073104 A1 | 4/2004 | Brun del Re et al. | |
| 2004/0254435 A1 | 12/2004 | Mathews et al. | |

FOREIGN PATENT DOCUMENTS

| | | |
|---|---|---|
| DE | 19749710 | 5/1999 |
| EP | 1428471 | 6/2004 |
| WO | 0213676 | 2/2002 |
| WO | 03048789 | 6/2003 |
| WO | 2004052190 | 6/2004 |

OTHER PUBLICATIONS

Searle A et al: "A direct comparison of wet, dry and insulting bioelectric recording electrodes; A comparison of bioelectrode performance" Physiological Measurement, Institute of Physics Publishing, Bristol, GB, vol. 21, No. 2, May 1, 2000, pp. 271-283.

Japanese Foreign Office Action mailed Aug. 10, 2010 for Japanese application 2007-547175.

* cited by examiner

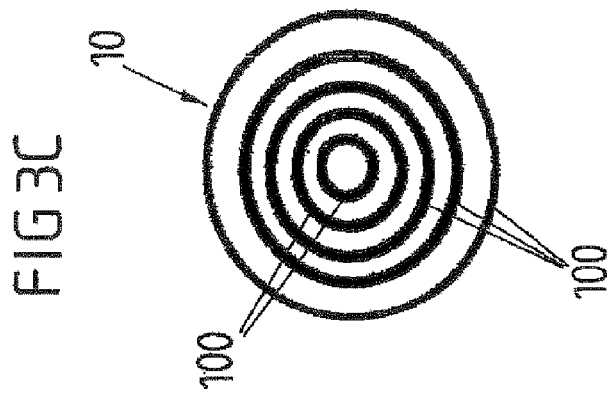
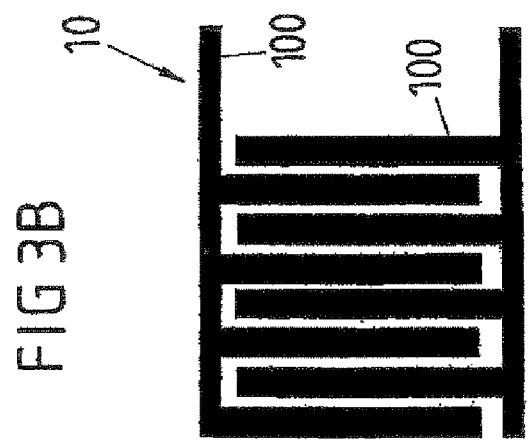
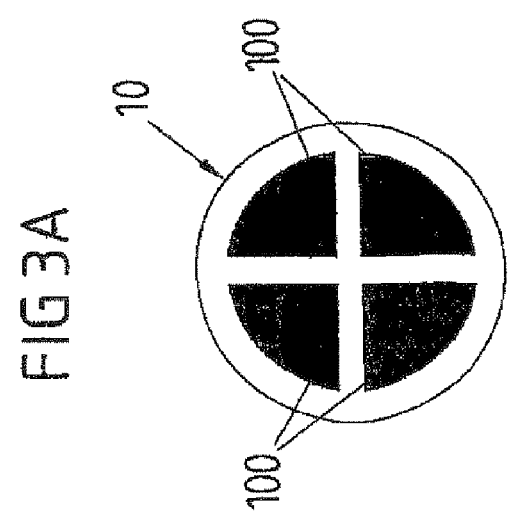

SENSOR SYSTEM AND METHODS FOR THE CAPACITIVE MEASUREMENT OF ELECTROMAGNETIC SIGNALS HAVING A BIOLOGICAL ORIGIN

The invention relates to a sensor system for the capacitive measurement of electromagnetic signals having a biobiological origin in accordance with the preamble of claim 1. The invention further relates to two methods for the capacitive measurement of electromagnetic signals having a biobiological origin, in particular by using the inventive sensor system.

Such a sensor system for the capacitive measurement of electromagnetic signals having a biobiological origin comprises a capacitive electrode device, an electrode shielding element, at least partially surrounding the electrode device, for shielding the electrode device against external electromagnetic interference fields and a signal processing device for processing electromagnetic signals that can be detected by means of the electrode device. Such sensor systems are normally used in medical technology, in particular in order to record signals having a biobiological origin for electroencephalograms (EEGs) and electrocardiograms (ECGs).

The capacitive measurement of the electromagnetic signals having a biobiological origin exhibits a range of advantages over the methods, known from the prior art, of using electrode devices galvanically coupled to a measurement object. Particularly in the case of the recording of an EEG, the frequently tiresome preparatory work of clearing hair from the measurement areas on the head of a test subject, and of reducing the electrical resistance of the scalp in these areas, for example by using a peeling agent in addition to the electrode gels required in any case, is eliminated. In the case of a capacitive coupling between a measurement area of the test subject and an electrode device, the electrical resistance of the coupling region is no longer relevant.

Capacitive sensor systems of the generic type are respectively disclosed in US 2003/0036691 A1 and WO 03/048789 A2.

Since the measurement signals having a biobiological origin that are to be determined are very small, the capacitive sensor systems known from the prior art and intended for measuring electromagnetic signals having a biobiological origin react sensitively to external electromagnetic interference fields despite the electrode shielding element that is present. Moreover, the problem arises that electrode capacitance that is necessarily formed by the arrangement of the sensor system at the measurement object between the capacitive electrode device of the sensor system and the measurement object, is changed by the movement of the measurement object relative to the electrode device, such that the electromagnetic signal detected by the electrode device has movement artefacts superposed on it and undergoes interference.

It is therefore the object of the present invention to provide an improved sensor system.

This object is achieved by means of a sensor system having the features of claim 1.

It is provided according to the invention that additional shielding means for shielding out external electromagnetic interference fields at least partially surround the electrode device and the electrode shielding element in three dimensions. The additional shielding means are designed in this case with different compartments, the signal processing device being arranged in one such compartment.

In this case, the feature of additional shielding means is to be understood within the scope of the present invention such that apart from the electrode shielding element additional shielding means are provided that are arranged separately therefrom in three dimensions. However, being separated in three dimensions is not to be interpreted to the effect that the additional shielding means are arranged without making mechanical and/or electrical contact with the electrode shielding element. Thus, it is by all means possible to provide an electrical contact between the shielding means and the electrode shielding element, for example for the purpose of ensuring an identical potential.

Apart from the electrode shielding element, the additional shielding means preferably surround the signal processing device at least partially. To this end, the additional shielding means can be designed both in such a way that the signal processing device is arranged in the region between the additional shielding means and the electrode shielding element, and in such a way that the additional shielding means at least partially surround both the electrode shielding element and the signal processing device.

The shielding means therefore shields the signal processing device from the signal source and from the electrode device in such a way that no parasitic galvanic, capacitive or inductive influences react on the source or on the electrode device.

A compact sensor system is provided in this way that is optimized with regard to shielding against external electromagnetic fields. The sensor system can be designed to be particularly compact by arranging the signal processing device adjacent to, that is to say in a fashion neighboring the electrode shielding element. The spatial proximity between the electrode device and signal processing device is attended by a range of advantages that is explained in yet more detail below.

For the purpose of the present invention, a signal processing device is regarded as any system that varies the incoming measurement signals, that is to say the system interacts with the measurement signals in such a way that the measurement signals have been varied upon passing through the system.

A preferred variant of the sensor system provides that the additional shielding means at least partially surround the signal processing device in such a way that the additional shielding means shield the electrode device against electromagnetic interference fields originating from the signal processing device.

Moreover, it is advantageous for the additional shielding means to be designed in such a way that the electrode device and the signal processing device are covered so as to define a solid angle range from which originating electromagnetic signals can be detected by means of the sensor system, without being substantially influenced by the shielding means and/or the electrode shielding element.

A further variant of the sensor system provides that the distance between the electrode shielding element and the electrode device and/or the geometry of the electrode shielding element and the electrode device and/or the dielectric properties of a filling in material arranged between the electrode shielding element and the electrode device are selected in such a way that the shielding capacitance between the electrode device and the electrode shielding element that results therefrom is small enough to minimize the coupling of noise signals of the signal processing device into the electrode device. It is ensured in this way that the signal path starting from the electrode device in the direction of the signal processing device functions essentially as a "one way street". The electrode device, which comprises at least one electrode element, is decoupled as far as possible in this way from the coupling of interference signals.

With regard to the geometry of the electrode device, it is, furthermore, advantageous for this to be selected in such a way that, together with a parasitic input impedance of the signal processing device, the electrode capacitance of the electrode device forms a highpass filter with a cut-off frequency adapted to an electromagnetic signal, having a biobiological origin, to be measured relative to a measurement object. This measure also contributes to the aforementioned decoupling of the electrode device from the signal processing device.

With regard to the geometry of the electrode device, it is preferred for this to be selected in such a way that input noise signals of the parasitic impedance of the signal processing device lie with their upper cut-off frequency below the lower cut-off frequency for the signals to be measured.

In one advantageous variant, the sensor system includes a housing. This housing encloses the additional shielding means. That is to say, the shielding means are designed as a component or components of the housing. To this end, the components can be designed in relation to the housing both as being of one piece and in a modular fashion. The electrode device is preferably coupled to the housing in such a way that the ohmic resistance between the electrode device and the housing is so high that a signal recorded capacitively by the electrode device is present at the input of the signal processing device without corruption.

The capacitive electrode device is advantageously arranged in the housing in such a way that there can be no occurrence of any connections to electrical sources that entail the risk of disruption of the electrode device or the signal processing device. To this end, the sensor system includes, in particular, an electrical insulator region for the electrical insulation of the electrode device from a signal source. Said region is advantageously designed in such a way that both the electrode shielding element and the shielding means are galvanically isolated from a signal source during measurement of said signal source. Moreover, the insulator region has material properties such that static charging of the insulator region by static environmental charges is minimized.

The signal processing device of the sensor system preferably includes an impedance converter as input stage. In one advantageous variant, the signal processing device has a difference amplifier. Particularly suitable in this case as difference signal is the signal of an external reference electrode that is in contact with the signal source.

A particularly preferred variant of the sensor system is distinguished by an integrated analog-to-digital conversion of the signals. To this end, the signal processing device comprises an analog-to-digital converter and a digital signal processor. Such processors are available at a satisfactory level of miniaturization such that an appropriately compact sensor system can also be provided with this functionality.

The input impedance of the signal processing device is advantageously to be selected in such a way that, together with the electrode capacitance of the electrode system, a highpass filter with a cut-off frequency adapted to an electromagnetic, having a biological origin, to be measured is formed. The electrode capacitance of the electrode system can, in particular, be set via the geometric parameters of the sensor system that have previously been explained.

A highpass filter is preferably provided in the signal processing device in such a way that a signal amplified in the signal processing device passes through the highpass filter such that DC voltage potentials are isolated from the dynamic measurement signal.

A further variant of the sensor system provides that the electrode device has a plurality of electrode elements for detecting electromagnetic signals having a biobiological origin. The plurality of the electrode elements acts in this case as a plurality of capacitive electrodes. A corresponding signal processing path is designed in the signal processing device for each of these electrode elements. It is also conceivable to provide a corresponding plurality of component signal processing devices.

The sensor system preferably has an electrical line device shielded to ground potential, for routing the measurement signal away from the sensor system. Further variants of the sensor system have means for line-conductive transmission and/or means for lineless transmission of the measurement device signals from the sensor system to a receiving spaced apart therefrom. Signals can be transmitted optically and/or electrically both for the line-conductive and for the lineless variants. For the optical variant, the sensor system has an optoelectronic transducer that is preferably of miniaturized design. Data can be transmitted both in free beam fashion and via optical waveguides such as optical fibers made from glasses or plastics.

It is advantageous to design the sensor system with a reference electrode. This reference electrode can be arranged next to the sensor system on a measurement object in such a way that the reference electrode provides a reference potential for the sensor system. The reference electrode is preferably designed in this case as an ohmic electrode.

However, it is possible in principle that the reference electrode is coupled to the measurement object in a resistive, conductive or capacitive fashion.

In addition to the provision of a reference potential, the reference electrode can also be used for coupling in an alternating signal by means of which a movement signal can be derived and it is therefore possible to compensate movement artefacts in the electromagnetic signal having a biobiological origin. In this case, the reference electrode fulfils a dual function, firstly that of providing the reference potential and secondly as a source for an alternating signal from which the movement signal can be derived and it is thereby possible to compensate movement artefacts. One or more reference electrodes can be used to feed in an alternating signal. When use is made of a number of reference electrodes, it is then possible to couple in alternating signals of different frequency, it being possible to separately compensate the movement artefacts of different electrode elements or electrode devices by means of each individual alternating signal.

The sensor system described above can be integrated in a multiplicity of measuring devices. By way of example, two that are suitable for recording EEGs and ECGs, in particular, are to be represented below.

One measuring device comprises a multiplicity of sensor systems that are arranged in a helmet-like or cap-like carrier device. This carrier device is designed in such a way that it can be slipped at least partially over the head of a test subject. In this case, it preferably has wearing properties for the test subject that preclude the measurements from becoming unpleasant over lengthy time intervals. That is to say, the weight, the uptake of, or the transmissive properties for, body moisture etc. should be optimized for wearing comfort with the aid of appropriate materials. It is conceivable that such a measuring device in the form of a previously explained cap is of great use, particularly for EEG diagnostics in emergency medicine. It is likewise conceivable that a person wearing such a cap interacts via his/her brain activity with systems to be controlled. These systems to be controlled can be computers, artificial limbs, robots or further machines or complex systems to be monitored or to be controlled by a human being. In this case, the cap would serve as interface between man and machine.

In the leisure sector, it would be possible in this way to control computer games entirely or partially. Thus, it would also be conceivable to use an interposed computer for mental interaction between a number of people.

A second measuring device comprises a multiplicity of sensor systems, the sensor systems being arranged on a flexible carrier device of two-dimensional design that can be fastened on the body of a test subject. This measuring device is therefore suitable, in particular, for recording ECGs. The statements previously made apply correspondingly with regard to wearing comfort.

The electrode devices and/or the housing and/or the additional shielding means and/or the electrode shielding elements are preferably produced from suitable flexible plastic in order to ensure that the measuring devices described previously have a flexibility adapted to the individual shape of head and body.

A further aspect of the present invention consists in that in the case of a capacitive measurement of electromagnetic signals having a biobiological origin, the problem arises that even very slight relative movements between the capacitive sensor system and a signal source lead to clear inference signals. Thus, periodically occurring mechanical pulse wave caused by the movement of the heart of an organism is already sufficient to influence the measurement signal. Moreover, clothing, hair etc. arranged between the sensor system and signal source also necessarily lead to so-called movement artefacts in the event of a movement of the signal source.

In order further to optimize the capacitive sensor systems known from the prior art, it is essential to minimize the influence of the movement artefacts on the measurement signals. This aspect of the invention is attained by means of the methods having the method steps in accordance with claims 29 and 33.

When use is made of a sensor system described above or of a measuring device described above, it is provided to arrange the sensor system or the measuring device at a measurement object. Thereafter, an electrical alternating signal is coupled into the measurement object in order to use the temporal change in the alternating signal detected via the electrode device to determine the electrode capacitance of the electrode device of the sensor system, or the electrode capacitance of the electrode devices of the measuring device. This determined electrode capacitance is taken into account in a concluding step when evaluating the measurement signals of the sensor system or of the measuring device.

It is likewise conceivable that the alternating signal coupled in can also be coupled out via a device other than the sensor systems used, and can be evaluated in order to determine electrode capacitance.

The coupling in is performed, for example, via a separate electrode, arranged on the measurement object for this purpose. This electrode can be designed both as an ohmic and as a capacitive electrode. The frequency of the alternating signal coupled in is usually removed by more than one order of magnitude from the frequencies of the physiologically relevant measurement signals. It is possible in a way that is technically known to undertake to couple the alternating signal out by means of a lock-in amplifier circuit.

The electrical alternating signal for determining the electrode capacitance of the electrode device of the sensor system or for determining the electrode capacitance of the electrode devices of the measuring device is preferably coupled into the measurement object via the electrode device or via a reference electrode cooperating externally with the sensor system or the measuring device. The reference electrode fulfils a dual function in this case.

The influence of the movement artefacts on a sensor system for measuring electromagnetic signals having a biobiological origin can therefore be minimized in entirely general fashion by means of a method having the following steps. Firstly, a capacitive sensor system suitable for measuring electromagnetic signals having a biobiological origin is arranged on a measurement object. An electrical alternating signal is then coupled into the measurement object, the alternating signal coupled in is then evaluated in order to determine the electrode capacitance of the sensor system, and then the electrode capacitance determined is finally taken into account when evaluating the measurement signals.

One of the previously named methods can preferably be carried out in such a way that a line-frequency interference signal is used as electrical alternating signal. The 50 or 60 Hz signal of the power supply is present in any case and would not firstly need to be generated by means of a device provided specifically therefor.

It is advantageous in this case to use the method to take account of the relative temporal change in the electrode capacitance of the electrode device of the sensor system or of the measuring device, and to derive the movement of the electrode device relative to the measurement object from the relative temporal change in the electrode capacitance. The movement thus determined can then be used to determine the movement artefacts superposed on the electromagnetic signals having a biological origin, and to compensate them.

A further method making use of a previously described sensor system and/or of a previously described measuring device provides the following steps. Firstly, the sensor system or the measuring device is arranged on a measurement object. Subsequently, the position parameters of the position of the sensor system or of the sensor systems are determined relative to the measurement object during the measurement, and the determined position parameters are taken into account for the purpose of compensating movement artefacts in the measurement signal.

All the sensor systems are provided with position measuring systems in order to determine the required position parameters. These position measuring systems determine the required relative position via a suitable measurement method. Suitable, in particular, to this end are optical, acoustic and piezoelectric devices and methods using these devices.

It is preferred to use robust methods of digital signal processing in order to process the electromagnetic signals that can then be measured with the aid of the electrode device. In particular, the data are filtered, both spatially and in the frequency domain. In this case, all the filters can also be adapted to the instantaneous signal characteristic during the measurement, if appropriate in real time. Furthermore, use is made, in particular, of univariate denoising methods that are based on the decomposition of the signals into arbitrary—including overdetermined or underdetermined—base systems such as, for example, wavelets, sinusoidal functions etc. Univariate denoising means that a measurement signal of the sensor system per se is denoised in a fashion isolated from the other, parallel measurement signals of the sensor system.

In particular, it is also possible to use techniques for describing signal dynamics (for example, autoregressive coefficients, nonlinear dynamic parameter extraction methods), or for describing synchronicity, in order to extract suitable signal features.

Furthermore, use is also made of multivariate methods for denoising. In this case, a number of measurement signals of the sensor system are denoised in a common process. These processes are based on a spatial projection of the measured data, for example with the aid of main component analysis, independent component analysis, projection pursuit techniques, sparse decomposition techniques or Bayesian subspace regularization techniques.

Use is made, furthermore, of projection techniques that take account of the geometry of the sensor system, in particular of the electrode device and of the shielding means and/or of the electrode shielding element such as, for example, beam-forming techniques, and laplace filters.

It is also possible to use variants of the said spatial projection methods that adapt to changes in the signal characteristics, so-called nonstationarities, if appropriate in real time. Nonstationarities are understood very generally as changes in the environmental conditions, for example, the addition or omission of noise sources, relative movements between sensor system and measurement object, variation in the physiological state of the measurement object etc.

Before beginning the actual measurement, it is optional to carry out a calibration measurement in the case of which signals are measured under specific conditions. This permits the use of monitored processing methods such as, for example, the common spatial patterns technique for spatial projection.

The calibration data are also used in order to carry out a model selection (determination of the best suited method and of the values of the settable parameters).

On the basis of these preprocessed, denoised data, use is made of suitable adaptive techniques for classification and regression that, as appropriate, adapt in real time to a possibly nonstationary signal characteristic. Examples of such methods are linear/nonlinear discriminance analysis, (kernel) Fisher discriminants, kernel-based learning methods (for example support vector machines, linear programming machines etc.), boosting, decision trees and neural networks.

Such techniques for classification and regression can be used, for example, to distinguish different (brain) states on the basis of the measured and preprocessed measurement signals, and thus to transmit information. It is also possible to predict states.

Further properties and advantages of the invention are explained in connection with the following drawings. In the drawings:

FIGS. 3a-3c show three variants relating to the multipartite configuration of the electrode device of the sensor system;

1. DESIGN OF THE SENSOR SYSTEM

Figure 1A:
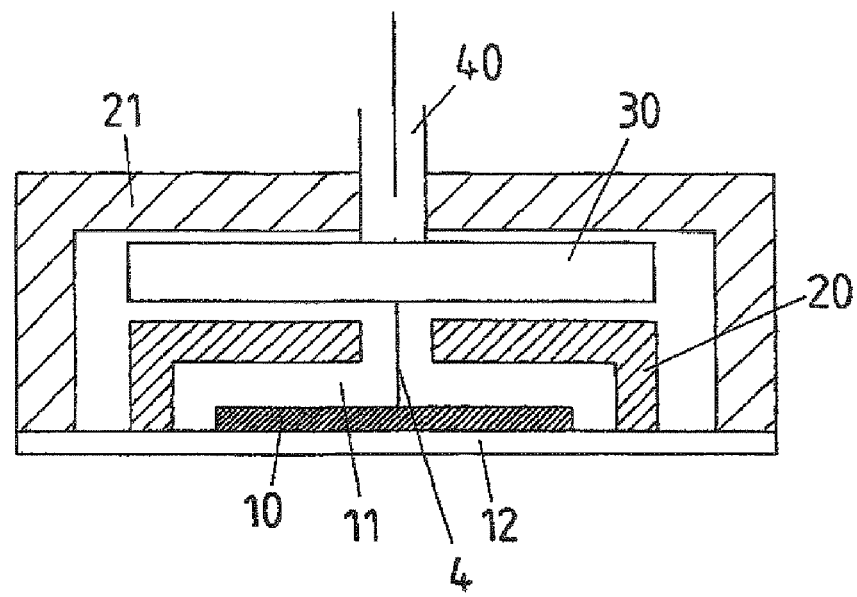
FIG. 1a shows a schematic cross section of a first exemplary embodiment of the sensor system according to the invention.

FIG. 1a shows a cross sectional illustration of a first embodiment of the sensor system according to the invention. This illustration is purely schematic and not true to scale. The electrode device 10 is arranged on an insulator element 12 of a dimensional design that acts as an insulator region. The electrode device 10 is surrounded essentially completely by an electrode shielding element 20 on the side of the insulator element 12 facing the electrode device 10. This electrode shielding element 20 is likewise fitted on the insulator element 12 and galvanically decoupled from the electrode device 10 by the insulator element 12.

The electrode shielding element 20 has an opening for leading through a signal line 4 emerging from the electrode device 10. This signal line 4 leads to a signal processing device 30 arranged outside the electrode shielding element 20. Both the signal processing device 30 and the electrode shielding element 20 are surrounded by additional shielding means 21 on the side of the insulator element 12 facing the electrode device 10. The additional shielding means 21 have a leadthrough for an electrical line device 40, screened to frame potential, for routing the measurement signal away from the sensor system.

The line device 40 shown can also be designed optically in the form of a light guide. In such a case, the signal processing device 30 includes a suitable electrooptic transducer. The light guide could then be designed both as an optical fiber and in optically integrated fashion. The use of a light guide as line device 40 would have the advantage that said light guide would require no shielding against external electromagnetic fields.

The insulator element 12 ensures, firstly, a galvanic decoupling of the electrode device 10. Secondly, it likewise serves the purpose of galvanic decoupling between the electrode shielding element 20 and the additional shielding means 21. In FIG. 1a, the electrode shielding element 20 is designed in cross section as two L-shaped limbs arranged lying opposite one another. Of course, a multiplicity of other geometric configurations for example with cambered sections of the electrode shielding element 20, are possible. It is especially important that the electrode shielding element 20 surrounds the electrode device 10 in such a way as to define a solid angle coming from which electromagnetic fields reach the electrode device 10 without experiencing attenuation caused by the electrode shielding element 20 in so doing.

Figure 1B:
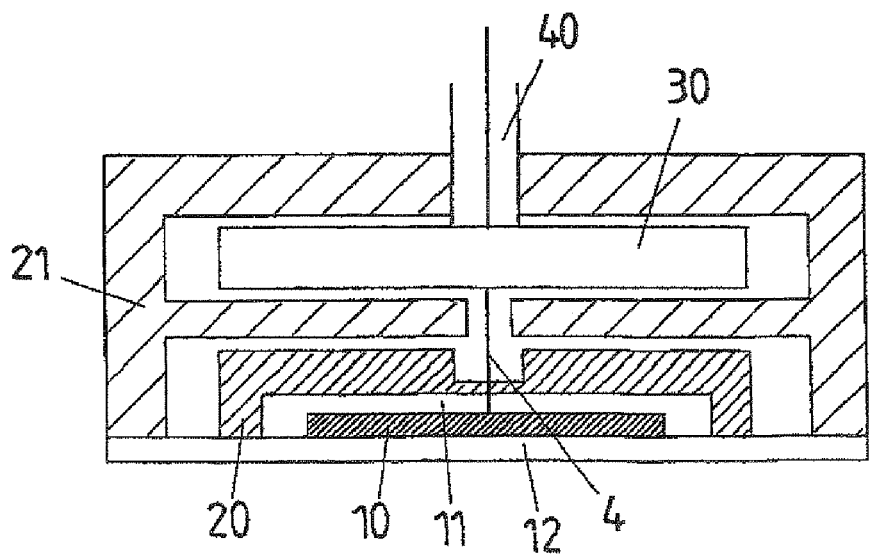
FIG. 1b shows a schematic cross section of a second embodiment of the sensor system according to the invention.

The preceding statements are valid mutatis mutandis with regard to the spatial configuration of the additional shielding means 21. As illustrated in FIG. 1b, it is possible to design the additional shielding means 21 with different compartments. In one such compartment, it is then possible to arrange the signal processing device 30 in such a way that the additional shielding means 21 also shield the electrode device 10 together with the electrode shielding element 20 against the signal processing device 30. The interference of electromagnetic fields generated in the signal processing device 30 is minimized in this way.

The existence of a multiplicity of geometric configurations both of the electrode shielding elements 20 and of the additional shielding means 21 is clear. This is associated, in particular, with the spatial configuration of the signal processing device 30. The signal processing device 30 does not imply that the latter must undertake the entire extent of the processing of the measurement signals. The signal processing can also run only partially in the illustrated signal processing device 30. Further signal processing devices arranged removed from the sensor system can be connected downstream of the illustrated signal processing device 30.

It is likewise valid with regard to the additional shielding means 21 that the latter need not necessarily be designed in one piece. A hybrid design comprising individual shielding elements is also possible. The passage openings for the signal lines 4 can likewise be of variable design in order to fulfil different requirements placed on shielding between signal processing device 30 and the electrode device 10.

Furthermore, the signal processing device 30 illustrated as a unitary component in FIGS. 1*a* and 1*b* can be constructed from a plurality of spatially separate subelements. Individual ones of these subelements, or all of them can be surrounded by the additional shielding means 21 in different or the same compartments.

Figure 2:
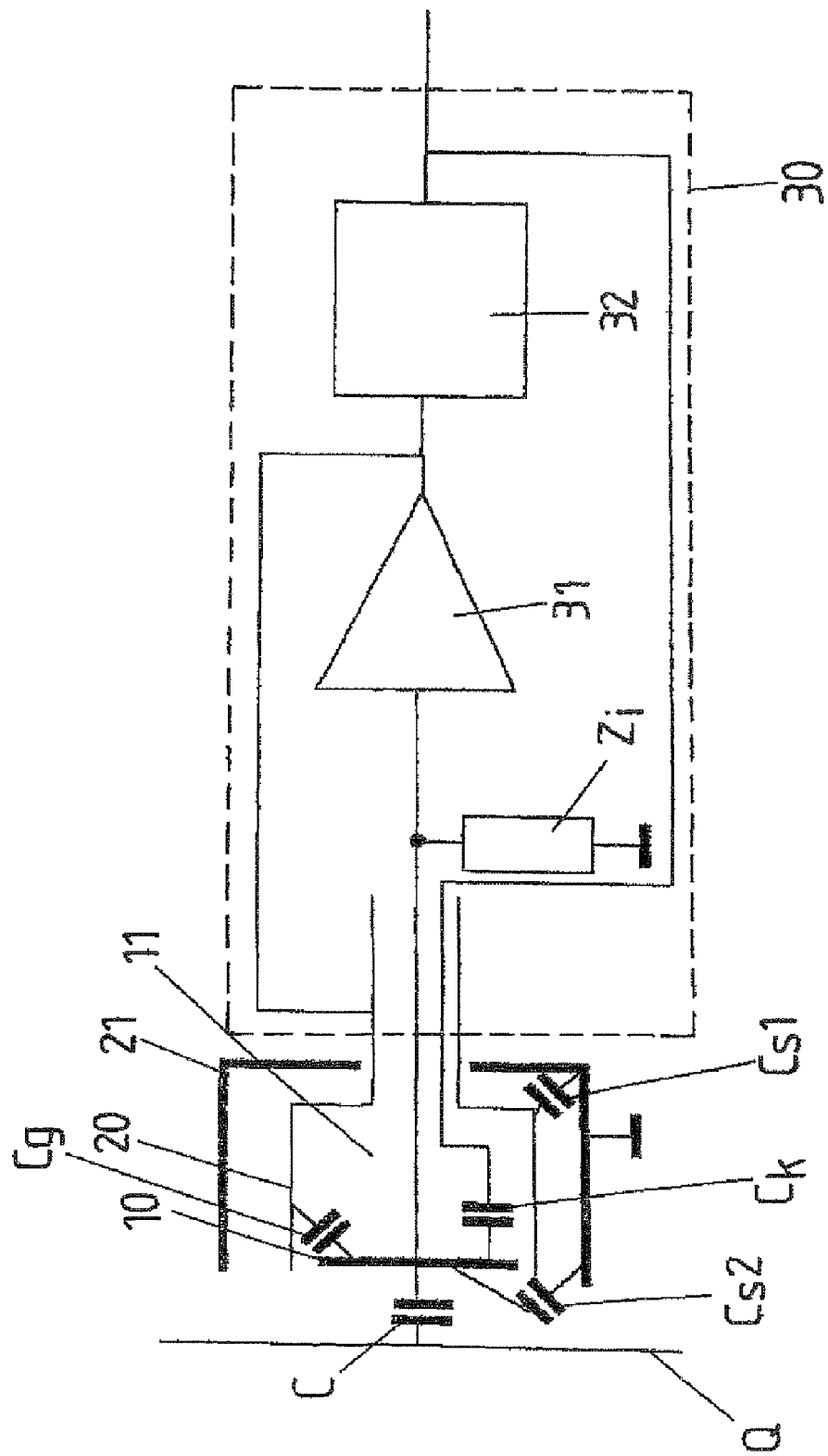
FIG. 2 shows a schematic equivalent circuit diagram of the sensor system according to the invention.

FIG. 2 shows a schematic equivalent circuit diagram of the sensor system according to the invention. The electrode device 10 has an electrode capacitance C with respect to a measurement object Q that acts as a source of electromagnetic signals having a biobiological origin.

An electric field, and the electrical potential of the source Q resulting therefrom, influences charge the capacitive electrode device 10 in accordance with the capacitance C thereof. This charge, which is itself also time-dependent given a time-dependent source Q, reaches an operational amplifier, acting as an impedance converter 31, of the signal processing device 30. This impedance converter 31 has an input impedance Zi. All the resistive, capacitive and inductive external contributions of the environment, and the internal input impedance of the impedance converter 31 are combined in this input impedance Zi. The external part of the impedance Zi is intended to have as small as possible a capacitive and inductive and as high as possible a resistive fraction. The impedance converter 31 converts its input signal to such a small output impedance that conventional circuits 32 can subsequently be used for the further signal processing. The output signal of the impedance converter 31 constitutes the potential for the electrode shielding element 20. This potential is denoted as guard potential in the case of commercially available guard electrode systems.

During the recording of the charge signal via the capacitor C, parasitic signals occur that can be coupled in via a parasitic shielding capacitor Cg acting between electrode device 10 and electrode shielding element 20, via a parasitic first shielding capacitor Cs1 acting between electrode shielding element 20 and the shielding means 21, and via a parasitic second shielding capacitor Cs2 acting between electrode device 10 and the shielding means 21.

It is therefore advantageous to set the previously described parasitic capacitors Cg, Cs1 and Cs2 by an appropriate adaptation of geometric parameters such as, in particular, the tolerances and the surface contour of the electrode shielding element and of the shielding means, the respective spacing between electrode device 10, electrode shielding element 20 and shielding means 21. Furthermore, the parasitic capacitor Cg can be influenced via the dielectric properties of the medium arranged between electrode device 10 and electrode shielding element 20. A corresponding statement is, of course, also valid for the parasitic capacitors Cs1 and Cs2.

As an alternative to feeding the processed signal back to the electrode device 10 via the compensation impedance Ck, the processed signal can be combined together with the output line of the impedance converter 31 in order to generate the potential for the electrode shielding element (guard potential) from a suitable logic operation. The parameters of the signal processing determine which type of signal logic operation (for example subtraction, addition etc.) is suitable for generating the guard potential. The dynamics range of the sensor system can also be increased in the way illustrated above.

Different variants of the design of the electrode device 10 are illustrated in FIGS. 3*a* to 3*c*. Each of the three variants shown comprises a plurality of electrode elements 100.

Four electrode elements are illustrated in FIG. 3*a* in the topology of symmetrically arranged quadrant elements. FIG. 3*b* shows a structure, interlocking in a finger-like fashion, of two comb-like electrode elements 100. In FIG. 3*c*, the electrode device 10 is designed in the form of five electrode elements 100 arranged as concentrically arranged rings of different diameter.

In the case of the multipartite design shown for the electrode device 10, there is a respective need for a corresponding plurality of signal lines and signal processing paths in order to ensure parallel signal processing in the signal processing device.

2. COMPENSATION OF STATIC CHARGES ON THE ELECTRODE DEVICE

The effect of external charges in the environment of the sensor system and of the electrode device 10 of the sensor system is to generate on the electrode device 10 or the individual electrode elements 100 of the electrode device 10 static charges that collect there and lead to static charging of the electrode device 10. Such static charging of the electrode device 10 or of the electrode elements 100 of the electrode device 10 greatly impairs the dynamic range of the sensor system for receiving the electromagnetic signals from the measurement object Q, and reduces the signal-to-noise ratio of the sensor system that can be achieved.

The detection of electromagnetic signals from the measurement object Q is attended by charge transfers on the electrode device 10. If an electromagnetic signal to be detected passes from the measurement object Q to the electrode device 10, the electromagnetic signal effects a charge transfer on the electrode device 10, induces a current and therefore a signal that is processed in the signal processing device 30. If, however, static charges are present on the electrode device 10 as a consequence of external charges in the environment of the sensor system, this has the effect that the dynamic range of the electrode device 10 is reduced for the electromagnetic signal from the measurement object Q that is actually to be detected and, in addition, interference signals are more strongly superposed on the electromagnetic signal.

In addition, the static charge located on the electrode device 10 exerts a substantial influence on the interference of the electromagnetic signal to be received from the measurement object Q, owing to movement artefacts caused by the movement of the electrode device 10 relative to the measurement object Q. The change in the signal received by the electrode device 10 as a function of the distance of the electrode device 10 from the measurement object Q can be described by the following equation:

$$\frac{\partial U}{\partial d} = \frac{1}{C}\frac{\partial Q}{\partial d} - \frac{Q}{C^2}\frac{\partial C}{\partial d} \qquad (1)$$

In equation (1), the first term represents the change in the voltage U of the electrode device 10 with the spacing d between the electrode device 10 and the Measurement object Q, the second term represents the change in the charge Q with the spacing d and the third term represents the change in the electrode capacitance C with the spacing d. In the case of a signal U detected by the electrode device 10 and not interfered with by movement artefacts, the second and third term of equation (1) must vanish, that is to say make no contribution, and so the signal U is independent of the change in the electrode capacitance C relative to the distance d between the electrode device 10 and the measurement object Q. As may be seen from equation (1), the third term is proportional to the charge Q collected on the electrode device 10. The suppression of the charge Q collected on the electrode device 10 is therefore attended by the reduction of movement artefacts interfering with the received signal.

In order to compensate the collection of static charges on the electrode device 10, a feedback is arranged in the sensor system between the output of the signal processing device 30 and the electrode device 10. In the case of the equivalent circuit diagram, as seen in FIG. 2, of the sensor system, a compensation impedance that is designed as a capacitor Ck is provided for this purpose. This compensation impedance acts between the electrode device 10 and the signal output of the signal processing device. This compensation impedance Ck, can, as illustrated in FIG. 2, be capacitive, but also resistive or inductive. The dynamic range of the sensor system can be enlarged by the provision of the compensation impedance Ck.

Figure 4:
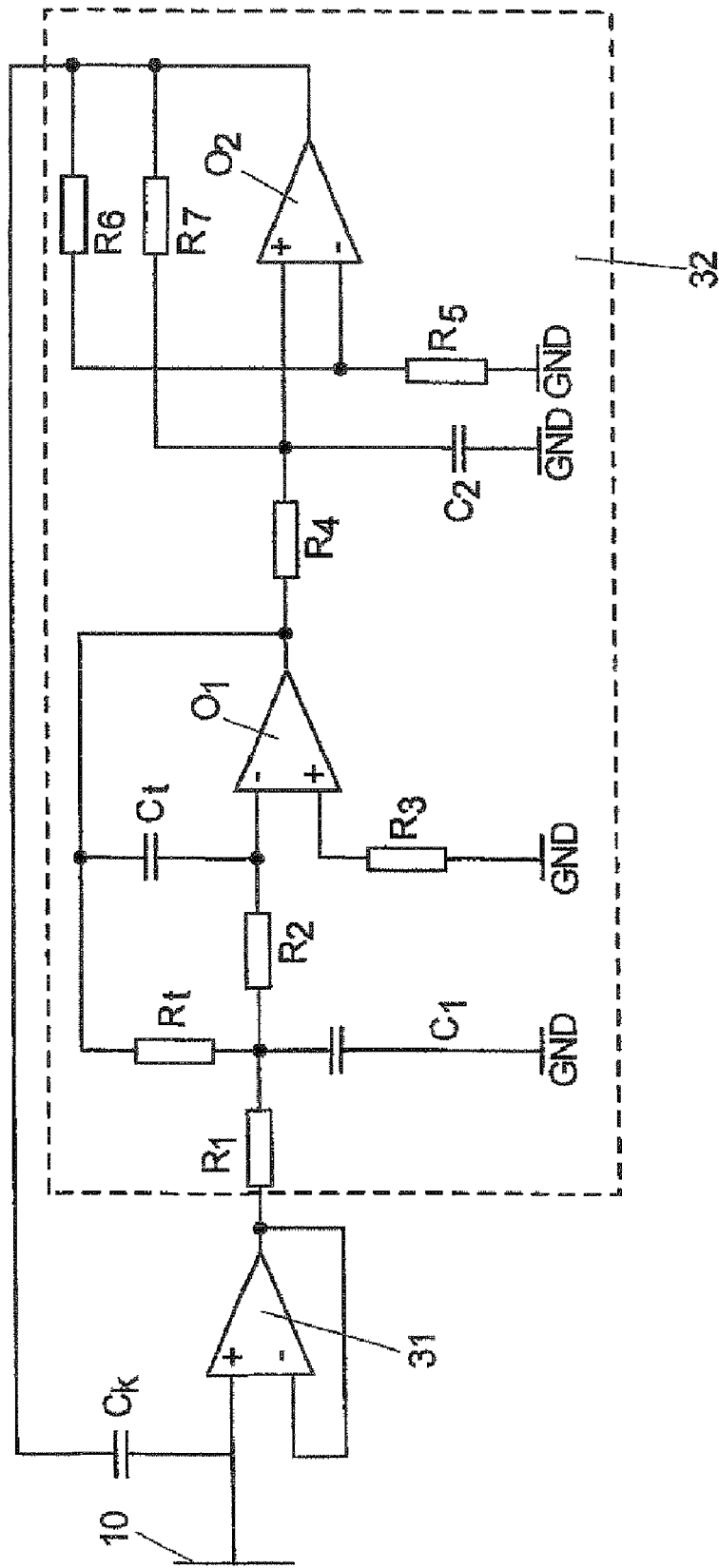
FIG. 4 shows a schematic equivalent circuit diagram of an embodiment of a compensation circuit for compensating static charges on the electrode device.

FIG. 4 illustrates a further embodiment of a compensation circuit using a compensation impedance Ck. The compensation circuit illustrated has an electrode device 10, an impedance converter 31 and a circuit 32 that serves for feeding the signal from the output of the signal processing device 30 back to the electrode device 10 via the compensation impedance Ck. The circuit 31 comprises two stages, of which the first stage, comprising the resistors R1, R2, R3 and Rt, the capacitors C1, Ct and the operation amplifier O1, constitutes a second order lowpass filter, and the second stage, comprising resistors R4, R5, R6, R7, capacitor C2 and the operation amplifier O2, constitutes a control circuit for feeding the signal back to the electrode device 10. A signal detected by the electrode device 10 is then led via the impedance converter 31 to the lowpass arrangement, filtered by the lowpass arrangement and fed back to the electrode device 10 via the control circuit and the compensation impedance formed by the capacitor Ck.

The effect of the compensation impedance Ck is that charge can be exchanged between the electrode device 10 and the output of the signal processing device 30. In this case, a lowpass-filtered output signal of opposite sign can be fed back to the electrode device 10 via the compensation impedance Ck, such that it is precisely the charge quantity opposite to the charge quantity collected on the electrode device 10 that is coupled into the electrode device 10. In this case, the cut-off frequency of the lowpass arrangement can be selected to be so small that the lowpass-filtered signal is essentially static in nature, and so it is also only the low frequency, essentially static components of the output signal that are fed back to the electrode device 10. Consequently, only the low frequency charge components of the electrode device 10 are compensated, these being (quasi) static in nature, that is to say only the substantially static charges that have collected on the electrode device 10. The cut-off frequency of the lowpass arrangement can in this case sensibly be of the order of magnitude of 200 mHz, and thus much below the frequency range of the electromagnetic signals to be detected from a measurement object Q.

A most far reaching complete suppression of the static charging of the electrode device 10 can be achieved by means of the compensation impedance Ck illustrated in FIG. 2 and in FIG. 4. It is thereby possible to improve the dynamic range of the electrode device 10, and to enlarge the achievable signal-to-noise ratio of the sensor system.

3. METHOD FOR CORRECTING MOVEMENT ARTEFACTS BY MEANS OF THE SENSOR SYSTEM

According to the invention, a method is provided by means of which it is possible to minimize the influence of movement artefacts on a measured electromagnetic signal from a measurement object Q as effected by a relative movement of the capacitive electrode device 10 with reference to the measurement object Q. In the case of the method according to the invention, it is provided in this case that a sensor system with an electrode device 10, or a measuring device having a multiplicity of sensor systems and electrode devices 10, is/are fitted on a measurement object Q, an electrical alternating signal is coupled into the measurement object via the electrode device 10, the alternating signal coupled in is evaluated, and the temporal change in the electrode capacitance C of the electrode device 10 of the sensor system is thereby determined. The determination of the electrode capacitance C is performed separately in this case for each electrode device 10 of each sensor system such that the movement of each electrode device 10 can be compensated separately.

The compensation is performed by taking account of the temporal change in the electrode capacitance and evaluating the measurement signals of each sensor system, and the movement artefacts caused by movement are thereby removed from the measurement signal by calculation.

Figure 5:
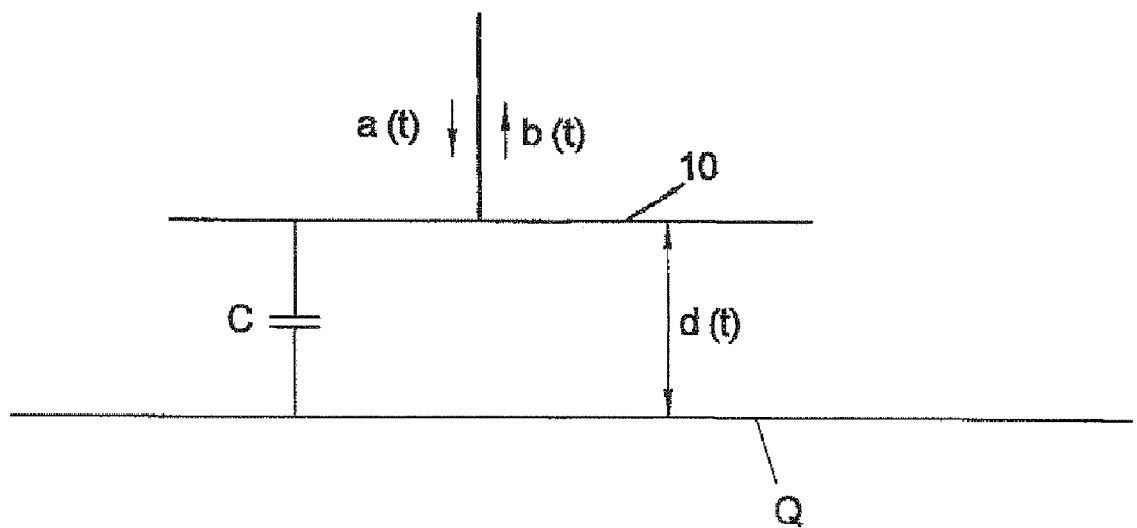
FIG. 5 shows a schematic of the arrangement of the electrode device at a distance from the measurement object.

A schematic sketch of the arrangement of an electrode device 10 on a measurement object Q is illustrated in FIG. 5. Here, the electrode device 10 lies at a distance d(t) from the measurement object Q, the distance d(t) being temporally variable, and therefore the capacitance C, formed by the electrode device 10 with the measurement object Q, is also temporally variable.

In order to determine the movement artefacts, a temporally variable alternating signal a(t) is applied to the electrode device 10, and the response signal b(t) of the alternating signal a(t) is measured. The alternating signal a(t) is in this case a carrier signal at a specific frequency, for example 300 Hz, while the response signal b(t) corresponds to the modulation of the alternating signal a(t) by the movement of the electrode device 10 relative to the measurement object Q. The movement of the electrode device 10 relative to the measurement object Q is correlated in this case with the temporal change in the electrode capacitance C, such that the information relating to the temporal change in the electrode capacitance C is contained in the response signal b(t) formed by the modulated alternating signal a(t).

In the arrangement illustrated in FIG. 5, the response signal b(t) corresponds to the amplitude modulation of the alternating signal a(t) as caused by the electrode capacitance C changing with the distance. However, it is also possible to conceive arrangements in which the alternating signal a(t) is modulated in frequency or phase by the changing electrode capacitance C, or by other known modulation methods, it being possible to this end to make use of known circuits in which the electrode capacitance C functions in each case as a modulating component.

It is also possible, as an alternative to feeding the alternating signal a(t) directly via the electrode device 10, to couple the alternating signal a(t) into the measurement object Q via a separate reference electrode, that is arranged at another site on the measurement object Q, and to detect via each electrode device 10 arranged on the measurement object Q a response signal b(t) that then corresponds to the modulated component of the alternating signal a(t) and contains for the respective electrode device 10 the information relating to the temporal change in the respective electrode capacitance C. This enables a simplification of the design of the sensor system, since in this case it is necessary only to receive signals via each electrode device 10, whereas an alternating signal a(t) is coupled in via a separate reference electrode. A feed path for feeding the alternating signal a(t) into each electrode device 10 is superfluous in this case, and so, as illustrated in FIG. 2, the sensor system need only have a receiving path, that is to say means 30, 31, 32 for receiving a signal. Such an electrode arrangement can, for example, be designed as illustrated in FIGS. 3a to c, in which case one of the electrode elements 100 would then serve as reference electrode, and the other electrode elements 100 as receiving electrodes.

The reference electrode can generally be fitted on the measurement object Q in resistive, inductive or capacitive fashion, in order to feed an alternating signal a(t) into the measurement object Q. It is also conceivable to use a number of reference electrodes that feed in alternating signals of different frequency, an electrode device 10 respectively receiving an alternating signal a(t) at a frequency from which it is then possible to draw conclusions relating to the movement of the respective electrode device 10 relative to the measurement object Q.

Figure 6:
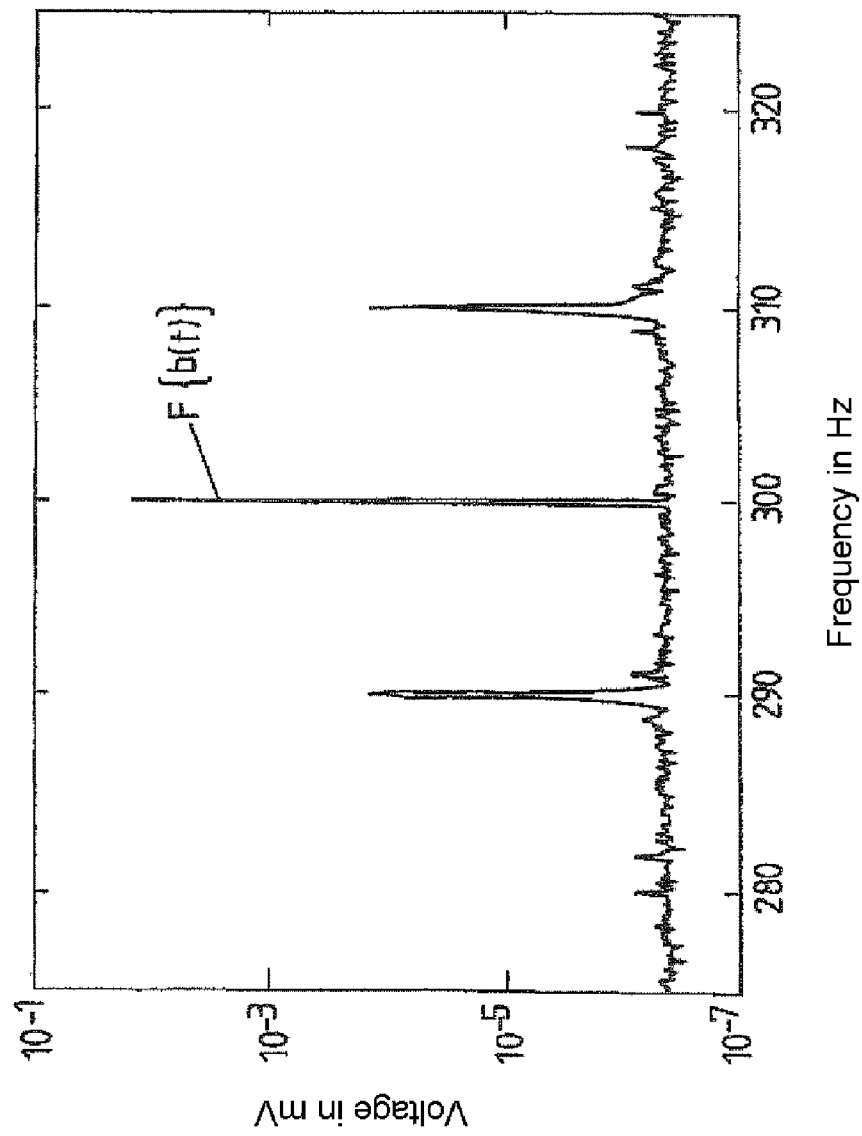
FIG. 6 shows a graph of the frequency spectrum of an alternating signal modulated by a movement of the electrode device.

FIG. 6 illustrates an example of a response signal b(t) received by an electrode device 10. Shown here is the frequency spectrum of the response signal b(t), which corresponds to the Fourier transformed F{b(t)} of the response signal b(t). In the case illustrated in FIG. 6, an alternating signal a(t) is coupled in via a reference electrode that is fitted on the measurement object Q in a resistive fashion, the electrode device 10 executing a movement at a frequency of 10 Hz relative to the measurement object Q. Correspondingly, the response signal b(t) illustrated in FIG. 6 has two sidebands around the frequency of the alternating signal a(t) of 300 Hz, specifically at 290 Hz and at 310 Hz, that are generated by the modulation of the alternating signal a(t) owing to the movement of the electrode device 10 relative to the measurement object Q.

Figure 7:
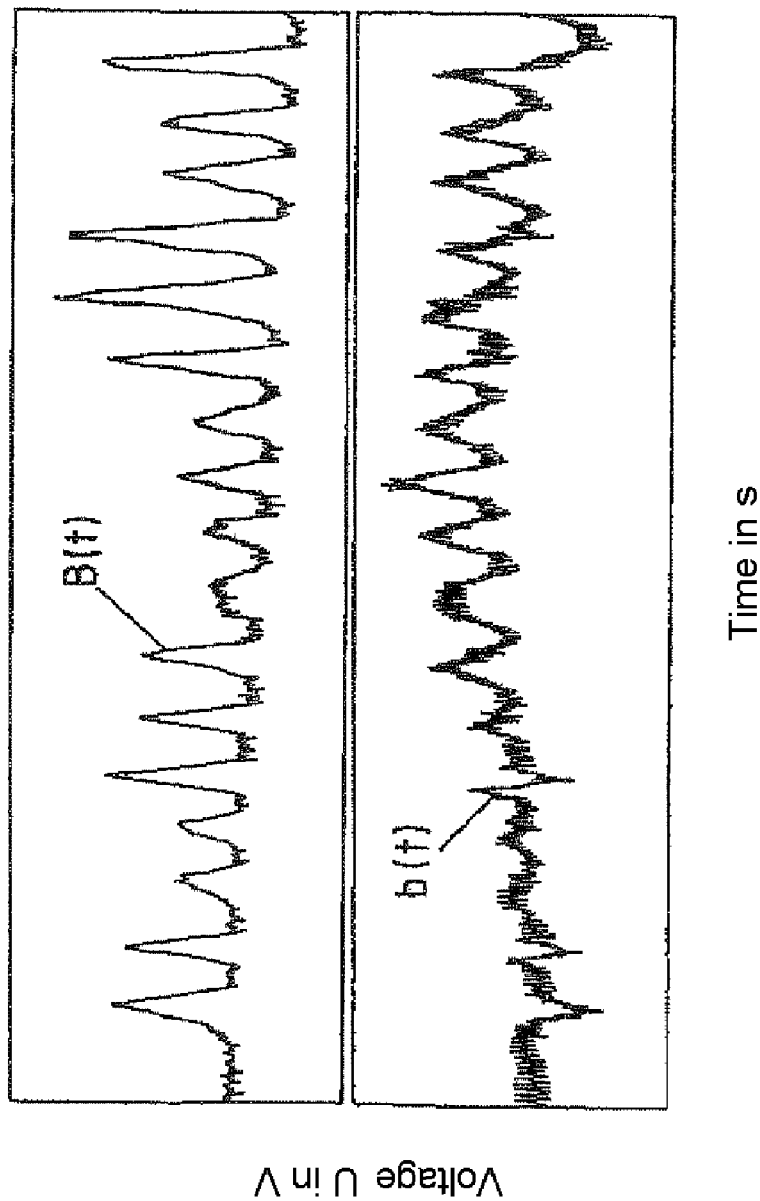
FIG. 7 shows a graph of an alternating signal modulated by a movement of the electrode device, and of the movement signal calculated from the modulated alternating signal.

FIG. 7 shows a measured response signal b(t) (bottom in FIG. 7) and a movement signal B(t) (top in FIG. 7) that is calculated from the response signal b(t) and is correlated with the temporal change in the electrode capacitance C, and therefore contains the information relating to the temporal change in the electrode device 10 relative to the measurement object Q. The movement signal B(t) is derived here from the response signal b(t) by subjecting the response signal b(t) to highpass filtering, and the components of the electromagnetic signal having a biobiological origin that is to be detected from the measurement object Q, which lie in a frequency range below the frequency of the alternating signal a(t), in this case 300 Hz, are suppressed. Subsequently, the highpass filtered response signal b(t) is demodulated, and so the component of the original alternating signal a(t) is removed from the response signal b(t) by calculation and the movement signal B(t) is thereby determined. Since the movement signal B(t) is correlated with the temporal change in the electrode capacitance C, and thus contains the information relating to the relative temporal change in the electrode capacitance C as a function of the movement of the electrode device 10 relative to the measurement object Q, the movement signal B(t) can be further processed and can be used with the aid of known signal processing algorithms to compensate the movement artefacts in the detected electromagnetic measurement signal having a biobiological origin. The compensation of the movement artefacts can be carried out in this case either in a post processing step downstream of the actual measurement, or else run in real time, given a correspondingly more powerful signal processing device 30, during the measurement for the purpose of direct compensation of the movement artefacts.

Figure 8:
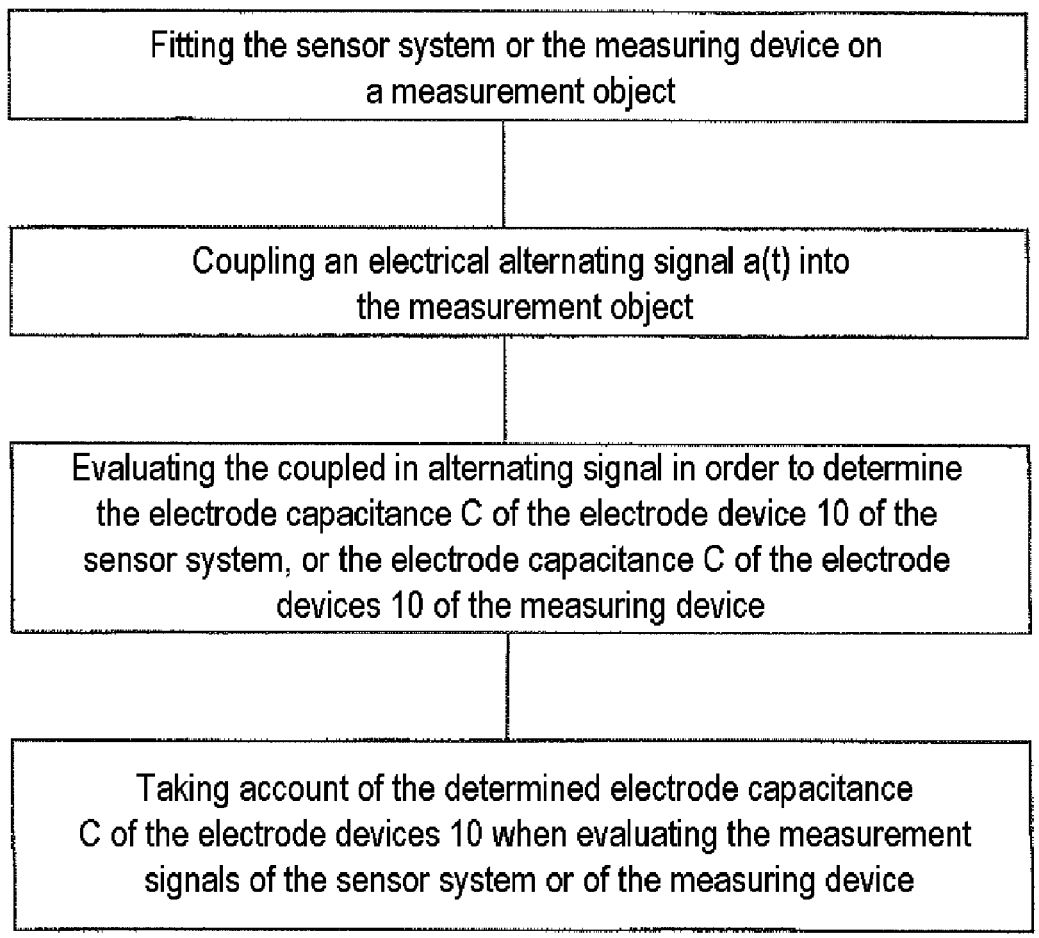
FIG. 8 shows a flowchart of a method relating to the method for minimizing the influence of movement artefacts by using a sensor system.

FIG. 8 shows the fundamental sequence of the method for minimizing the influence of movement artefacts by using the sensor system according to the invention, in the case of which the change in the electrode capacitance C of the electrode device 10 is taken into account when evaluating the measurement signals of the sensor system or of the measuring device.

Figure 9:
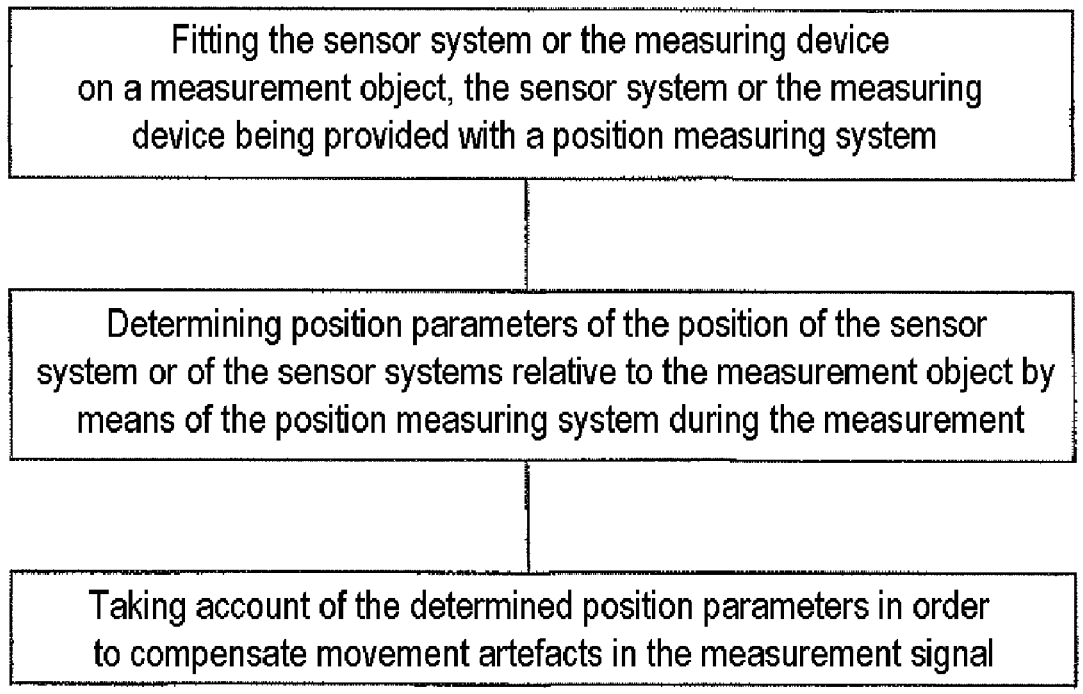
FIG. 9 shows a flowchart of a second method relating to the method for minimizing the influence of movement artefacts by using a sensor system.

The fundamental sequence of a further method for minimizing the influence of movement artefacts is illustrated in FIG. 9. In this method, the sensor system or the measuring device is firstly arranged on a measurement object, the sensor system or the measuring device being provided with a position measuring system for determining the position of the sensor system or measuring device. Subsequently, the position parameters of the position of the sensor system or the sensor systems are determined relative to the measurement object during the measurement, and the determined position parameters are taken into account to compensate movement artefacts in the measurement signal.

What is claimed is:

1. A method for minimizing the influence of movement artefacts to measure electromagnetic signals having a biobiological origin, comprising the following steps:
    fitting a sensor system or a measuring device on a measurement object,
    coupling an electrical alternating signal into the measurement object,
    evaluating the coupled in alternating signal in order to determine the electrode capacitance of the electrode device of the sensor system, or the electrode capacitance of the electrode devices of the measuring device, and
    taking account of the determined electrode capacitance of the electrode devices when evaluating the measurement signals of the sensor system or of the measuring device, wherein the relative temporal change in the electrode capacitance of the electrode device of the sensor system or of the measuring device is taken into account, a movement signal of the electrode device relative to the measurement object is derived from the relative temporal change in the electrode capacitance, and the interfering movement artefacts superposed on the electromagnetic signals having a biobiological origin are compensated by means of the determined movement signal.

2. The method as claimed in claim 1, in which the electrical alternating signal for determining the electrode capacitance of the electrode device of the sensor system, or for determining the electrode capacitance of the electrode devices of the measuring device are coupled into the measurement object via the electrode device or via an external reference electrode cooperating with the sensor system or the measuring device.

3. The method as claimed in claim 1, wherein a line frequency interference signal is used as electrical alternating signal.

4. The method according to claim 1, using a sensor system for the capacitive measurement of electromagnetic signals having a biobiological origin, the sensor system comprising:
    a capacitive electrode device,
    an electrode shielding element, at least partially surrounding the electrode device, for shielding the electrode device against external electromagnetic interference fields, and a signal processing device for processing electromagnetic signals that can be detected by means of the electrode device, wherein additional shielding means for shielding out external electromagnetic interference fields at least partially surround the electrode device and the electrode shielding element in three dimensions, the additional shielding means being designed with different compartments, and the signal processing device being arranged in one such compartment.

5. The method of claim 4, wherein the shielding means surround the signal processing device at least partially.

6. The method of claim 4, wherein the signal processing device is arranged adjacent to the electrode shielding element.

7. The method of claim 4, wherein the shielding means surround the signal processing device at least partially in such a way that the shielding means also act as an electromagnetic shield between the signal processing device and electrode device.

8. The method of claim 4, wherein the shielding means cover the electrode device and the signal processing device in such a way as to define a solid angle range from which originating electromagnetic signals can preferably be detected by means of the sensor system.

9. The method of claim 4, wherein the distance between the electrode shielding element and the electrode device and/or the geometry of the electrode shielding element and of the electrode device and/or the dielectric properties of a filling in material arranged between the electrode shielding element and the electrode device are selected in such a way that the shielding capacitance resulting therefrom is sufficiently small to minimize the coupling of noise signals of the signal processing device into the electrode device.

10. The method of claim 4, wherein the geometry of the electrode device is selected in such a way that, together with a parasitic leakage resistance of the signal processing device, the electrode capacitance of the electrode device forms a highpass filter with a cut-off frequency adapted to an electromagnetic signal, having a biobiological origin, to be measured relative to a measurement object.

11. The method of claim 10, wherein the geometry of the electrode device is selected in such a way that noise signals of the parasitic input resistance of the signal processing device lie with their upper cut-off frequency below the lower cut-off frequency for the signals to be measured.

12. The method of claim 11, wherein the insulator region has material properties such that static charging of the insulator region by static environmental charges is minimized.

13. The method of claim 4, wherein the sensor system has a housing enclosing the shielding means, the electrode device being arranged in the housing in such a way that the ohmic resistance between the electrode device and the housing is so high that a capacitively recorded signal is present at the input of the signal processing device without corruption.

14. The method of claim 4, wherein the sensor system has an electrical insulator region for the electrical insulation of the electrode device in such a way that both the electrode shielding element and the shielding means are galvanically isolated from a signal source during measurement of said signal source.

15. The method of claim 4, wherein the signal processing device has an input stage designed as impedance converter.

16. The method of claim 4, wherein the signal processing device has a difference amplifier, it being possible to process the signal of an external reference electrode as difference signal.

17. The method of claim 4, wherein the signal processing device comprises an analog-digital converter and a digital signal processor.

18. The method of claim 4, wherein the signal processing device is shielded from a signal source and from the electrode device by the shielding means such that no parasitic galvanic, capacitive or inductive influences react on the signal source or on the electrode device.

19. The method of claim 4, wherein a feedback of processed signals to the electrode device is provided via a compensation impedance implemented in a capacitive, resistive or inductive fashion.

20. The method of claim 4, wherein the input impedance of the signal processing device is selected in such a way that, together with the electrode capacitance of the sensor system, a highpass filter with a cut-off frequency adapted to an electromagnetic signal, having a biobiological origin, to be measured is formed.

21. The method of claim 4, wherein a signal amplified by the signal processing device passes through a highpass filter in order to isolate DC voltage potentials from the dynamic measurement signal.

22. The method of claim 4, wherein the electrode device has a plurality of electrode elements for detecting electromagnetic signals having a biobiological origin, the signal processing device being designed as a corresponding plurality of parallel connected component signal processing devices.

23. The method of claim 4, wherein an electrical line device is shielded to ground potential, for routing the measurement signal away from the sensor system.

24. The method of claim 4, wherein the sensor system has means for line-conductive transmission and/or means for lineless transmission of the measurement signals from the sensor system to a receiving device spaced apart therefrom.

25. The method of claim 4, wherein the measuring device having has a multiplicity of sensor systems in accordance with claim 4, in which the sensor systems are arranged in a helmet-like or cap-like carrier device that can be at least partially slipped over the head of a test subject.

26. The method of claim 4, wherein the measuring device has a multiplicity of sensor systems in accordance with claim 4, in which the sensor systems are arranged on a flexible carrier device of two-dimensional design that can be fastened on the body of a test subject.

27. The method of claim 4, wherein the sensor system cooperates with a reference electrode that can be fastened next to the sensor system on a measurement object, and provides a reference potential for the sensor system.

28. The method of claim 27, wherein the reference electrode is coupled to the measurement object in a resistive, conductive or capacitive fashion.

29. The method of claim 27, wherein the reference electrode is used for coupling in an alternating signal by means of which a movement signal can be derived and it is therefore possible to compensate movement artefacts in the electromagnetic signal having a biobiological origin.

30. The method of claim 27, wherein one or more reference electrodes are used.

31. The method of claim 30, wherein a number of reference electrodes are used for coupling in alternating signals of different frequency, it being possible to compensate the movement artefacts of different electrode elements or electrode devices by means of each individual alternating signal.

* * * * *

UNITED STATES PATENT AND TRADEMARK OFFICE
CERTIFICATE OF CORRECTION

| | |
|---|---|
| PATENT NO. | : 8,193,821 B2 |
| APPLICATION NO. | : 11/722495 |
| DATED | : June 5, 2012 |
| INVENTOR(S) | : Mueller et al. |

Page 1 of 1

It is certified that error appears in the above-identified patent and that said Letters Patent is hereby corrected as shown below:

On the Title page, item (73), under "Assignee", in Column 1, Line 1,
delete "Fraunhoffer-Gesellschaft zur Foerderung der Angewandten Forschung E.V." and insert
-- Fraunhofer-Gesellschaft zur Foerderung der Angewandten Forschung E.V. --, therefor.

Signed and Sealed this
Fourteenth Day of August, 2012

David J. Kappos
*Director of the United States Patent and Trademark Office*